(12) United States Patent
Roeder et al.

(10) Patent No.: US 8,574,285 B2
(45) Date of Patent: Nov. 5, 2013

(54) INTRALUMINAL DEVICE WITH IMPROVED TAPERED BEAMS

(75) Inventors: Blayne A. Roeder, Lafayette, IN (US); Alan R. Leewood, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1377 days.

(21) Appl. No.: 11/454,303

(22) Filed: Jun. 15, 2006

(65) Prior Publication Data

US 2007/0021824 A1 Jan. 25, 2007

Related U.S. Application Data

(60) Provisional application No. 60/690,776, filed on Jun. 15, 2005.

(51) Int. Cl.
*A61F 2/06* (2013.01)

(52) U.S. Cl.
USPC ........................................................ 623/1.15

(58) Field of Classification Search
USPC ........................................ 623/1.15, 1.18, 1.2
See application file for complete search history.

(56) References Cited

U.S. PATENT DOCUMENTS

| | | | |
|---|---|---|---|
| 4,893,623 A | 1/1990 | Rosenbluth | |
| 5,861,027 A | 1/1999 | Trapp | |
| 6,190,406 B1 | 2/2001 | Duerig et al. | 623/1.2 |
| 6,540,774 B1 | 4/2003 | Cox | |
| 2001/0032011 A1 | 10/2001 | Stanford | |
| 2002/0095140 A1 | 7/2002 | Lootz et al. | |

FOREIGN PATENT DOCUMENTS

| | | |
|---|---|---|
| EP | 1 184 007 A | 3/2002 |
| EP | 1184007 A2 * | 3/2002 |
| WO | WO 99/16387 A | 4/1999 |
| WO | WO 02/24111 A | 3/2002 |

OTHER PUBLICATIONS

U.S. Appl. No. 11/455,274, filed Jun. 15, 2006, Roeder et al.
International Search Report from PCT/US2006/023464 dated Oct. 4, 2006, 5p.

* cited by examiner

*Primary Examiner* — Gary Jackson
*Assistant Examiner* — Erin Colello
(74) *Attorney, Agent, or Firm* — Brinks Hofer Gilson and Lione

(57) ABSTRACT

A strut, or beam, is provided for intraluminal devices. Strain which is introduced into a stent or other intraluminal device is distributed more evenly along the length of the improved strut by maintaining a substantially constant strain level along the length of an end portion. This may increase fatigue life or improve the performance of devices using the improved strut. The strain along the length of the end portion may be maintained substantially constant by varying a section property of the strut, including the width, thickness, cross-sectional area, material property or other characteristic of the end portion.

9 Claims, 4 Drawing Sheets

INTRALUMINAL DEVICE WITH IMPROVED TAPERED BEAMS

RELATED APPLICATIONS

This application claims priority to U.S. Provisional Application No. 60/690,776, filed Jun. 15, 2005, which is hereby incorporated by reference herein.

This application is related to U.S. patent application Ser. No. 11/455,274, incorporated herein by reference and entitled Intraluminal Device With Unsymmetric Tapered Beams, filed by the same inventors on the same day as the present application.

BACKGROUND

The present invention relates generally to medical devices and more particularly to intraluminal devices suitable for percutaneous transluminal delivery into a body.

A variety of intraluminal devices are known to those in the medical arts, including stents, stent-grafts, filters, occluders, artificial valves and other endoprosthetic devices. For example, stents have now become a relatively common device for treating a number of organs, such as the vascular system, colon, biliary tract, urinary tract, esophagus, trachea and the like. Stents are useful in a variety of medical procedures and are often used to treat blockages, occlusions, narrowing ailments and other related problems that restrict flow through a passageway. Stents are also useful in treating various types of aneurysms, either in the form of a stent-graft or to retain an embolization device within the aneurysm.

The above-described examples are only some of the applications in which intraluminal devices are used by physicians. Many other applications for intraluminal devices are known and/or will be developed in the future. For example, in addition to the use of stents and stent-grafts to treat vascular stenosis and aneurysms, similar procedures may also be used to deploy vascular filters, occluders, artificial valves and other endoprosthetic devices.

In order to deliver a stent through narrow passageways, the stent is typically collapsed into a delivery configuration with a small diameter. The collapsed stent structure may then be inserted into a sheath which retains the stent in the delivery configuration until it is released. Because the stent must be significantly collapsed in this configuration, a large strain is introduced into the stent structure. Since a typical stent structure is only collapsed into the delivery configuration one time or a minimal number of times, it is generally considered that the stent structure can accommodate a large strain level in this application without resulting in permanent damage to the stent structure.

Once the stent is released at the site of implantation, the stent structure expands and contacts the lumen wall. In this process, a large portion of the strain is relieved. However, in most cases it is desirable for the stent to exert at least a minimum radial force against the lumen wall after implantation. Therefore, the size of stent which is usually selected for a particular use has a fully expanded, or relaxed, diameter that is larger than the lumen wall in which the stent will be implanted. As a result, the strain in the stent structure is not completely relieved after implantation, and the stent structure remains permanently under a lower amount of strain.

One problem with current stent structures is that they may weaken and/or fail due to fatigue in the bends that interconnect the struts. Fatigue may occur because stents are frequently implanted into organs like arteries that pulse in diameter each time that the heartbeats. As a result, the stent structure expands and contracts a small amount with each heartbeat. With each expansion and contraction of the stent, the strain in the stent structure cycles between two different strain levels. Over many strain cycles, the structure of the stent may eventually become permanently damaged. One risk is that fatigue damage may cause bends in the stent structure to fracture and break. This may result in undesirable tissue damage and may reduce the effectiveness of the stent. Moreover, fatigue behavior, in addition to considerations of the high initial strain introduced into the stent during delivery, may limit the design choices available to makers of stents. For example, stents with longer struts are sometimes used in order to minimize the strain on the bends. However, stents with longer struts may be subject to undesirable tissue prolapse after implantation, in which tissues of the lumen wall grow around and encapsulate the stent structure. In certain applications, stents with shorter struts may be desirable to minimize tissue prolapse and to increase the radial force exerted on the lumen wall. However, stents with shorter struts may be subject to higher strain levels which may damage the structure of the stent.

BRIEF SUMMARY

A strut, or beam, is described for intraluminal devices. The strut includes an end portion that is connected to a bend and connected to a middle portion. The end portion is formed in part by a top side surface and a bottom side surface. A width of the end portion is defined by the top side surface and the bottom side surface. The end portion is further defined by a section property extending along the length of the end portion. The width of the end portion and/or the section property is varied to maintain a substantially constant strain level along the length of the end portion.

The improvement over the prior art relates to an improved strain distribution along the length of a beam used in intraluminal devices. In prior art intraluminal devices, the strain substantially varies along the length of the beam when a bending force is applied to the beam. This is undesirable because certain parts of the beam will experience higher strain levels, which may lead to fatigue failures or require more robust beam designs. By contrast, the invention maintains a substantially constant strain level along the length of the beam. Thus, for example, while the strain levels along the top and bottom side surfaces may be different from each other, the strain level along the length of the top side surface is substantially constant. Similarly, the strain level along the bottom side surface is substantially constant along the length thereof. Therefore, at least one advantage of the invention is that the overall strain introduced into the beam is distributed more evenly across the structure. This may improve fatigue life by reducing regions of high strain seen in prior art devices and/or by providing a more efficient beam design. Additional details and advantages are described below in the detailed description.

The invention may include any of the following aspects in various combinations and may also include any other aspect described below in the written description or in the attached drawings.

An intraluminal device, comprising:

a beam comprising an end portion connected to a bend adjacent a first end and connected to a middle portion adjacent a second end, the beam and the bend being made from an elastic material;

the end portion comprising a first side surface disposed toward the bend and a second side surface disposed away from the bend;

a first distance between the first side surface and the second side surface at the first end being greater than a second distance between the first side surface and the second side surface at the second end; and wherein a width defined by the first side surface and the second side surface is proportional to a distance from the second end raised to a power between 0.6 and 0.4.

The intraluminal device wherein the width is proportional to a distance from the second end raised to a power between 0.55 and 0.45.

The intraluminal device wherein the width is proportional to a distance from the second end raised to a power of 0.5.

The intraluminal device wherein the beam comprises a strut in a stent.

The intraluminal device wherein the beam is connected to another beam, the beams being collapsible into a delivery configuration adapted to pass through a lumen and a delivered configuration adapted to engage a wall of the lumen, an included angle defined by the beams being adapted to be less than 5° in the delivery configuration.

The intraluminal device wherein the beam is made from a superelastic material.

The intraluminal device wherein the superelastic material is nitinol.

The intraluminal device wherein the beam is made from a non-superelastic metal.

The intraluminal device wherein the width is proportional to a distance from the second end raised to a power of 0.5, the beam comprising a strut in a stent made from a superelastic material, and the strut is connected to another strut, the struts being collapsible into a delivery configuration adapted to pass through a lumen and a delivered configuration adapted to engage a wall of the lumen, an included angle defined by the struts being adapted to be less than 5° in the delivery configuration.

An intraluminal device, comprising:
a beam comprising an end portion connected to a bend adjacent a first end and connected to a middle portion adjacent a second end, the beam and the bend being made from an elastic material;
the end portion comprising a first side surface disposed toward the bend and a second side surface disposed away from the bend, the first side surface and the second side surface defining a width, w(x), therebetween at a distance, x, from the second end;
an outer surface and an inner surface defining a thickness, t, therebetween; and
wherein an area moment of inertia of the cross-section of the end portion is defined substantially by the formula $I=tw(x)^2$.

The intraluminal device wherein the beam comprises a strut in a stent.

The intraluminal device wherein the beam is connected to another beam, the beams being collapsible into a delivery configuration adapted to pass through a lumen and a delivered configuration adapted to engage a wall of the lumen, an included angle defined by the beams being adapted to be less than 5° in the delivery configuration.

The intraluminal device wherein the beam is made from a superelastic material.

The intraluminal device wherein the superelastic material is nitinol.

The intraluminal device wherein the beam is made from a non-superelastic metal.

The intraluminal device wherein the beam comprises a strut in a stent made from a superelastic material, the strut being connected to another strut, the struts being collapsible into a delivery configuration adapted to pass through a lumen and a delivered configuration adapted to engage a wall of the lumen, an included angle defined by the struts being adapted to be less than 5° in the delivery configuration.

An intraluminal device, comprising:
a beam comprising an end portion connected to a bend adjacent a first end and connected to a middle portion adjacent a second end, the beam and the bend being made from an elastic material;
the end portion comprising a first side surface and a second side surface; one of the first side surface and the second side surface being disposed toward the bend and the other of the first side surface and the second side surface being disposed away from the bend;
a section property extending between the first end and the second end and being defined by at least a cross-sectional area and a material property; and
wherein the section property is varied between the first end and the second end, a first strain thereby being substantially constant along the first side surface between the first end and the second end.

The intraluminal device wherein the first strain varies between the first end and the second end within a range of no more than 3% when the beam is compressed into a delivery configuration.

The intraluminal device wherein the first strain is less than at least 4% between the first end and the second end when the beam is compressed into a delivery configuration.

The intraluminal device wherein the first side surface is disposed toward the bend.

The intraluminal device wherein the cross-sectional area is varied without varying the material property.

The intraluminal device wherein a first distance between the first side surface and the second side surface at the first end is greater than a second distance between the first side surface and the second side surface at the second end, a thickness of the beam being substantially constant between the first end and the second end.

The intraluminal device wherein the beam comprises a strut in a stent.

The intraluminal device further comprising a second strain along the second side surface, the second strain being substantially constant between the first end and the second end.

The intraluminal device wherein the beam is connected to another beam, the beams being collapsible into a delivery configuration adapted to pass through a lumen and expandable to a delivered configuration adapted to engage a wall of the lumen, an included angle defined by the beams being adapted to be less than 5° in the delivery configuration, and a total range of operable strain for the first strain and the second strain being less than 0.4% in the delivered configuration.

The intraluminal device wherein the beam is made from a superelastic material.

The intraluminal device wherein the superelastic material is nitinol.

The intraluminal device wherein the beam is made from a non-superelastic metal.

The intraluminal device wherein the cross-sectional area is varied without varying the material property, a first distance between the first side surface and the second side surface at the first end being greater than a second distance between the first side surface and the second side surface at the second end.

The intraluminal device wherein the beam comprises a strut in a stent made from a superelastic material, the strut being connected to another strut, the struts being collapsible into a delivery configuration adapted to pass through a lumen and a delivered configuration adapted to engage a wall of the lumen, an included angle defined by the struts being adapted to be less than 5° in the delivery configuration, and a total range of operable strain for the first strain and the second strain being less than 0.4% in the delivered configuration.

The intraluminal device further comprising a second strain along the second side surface, the second strain being substantially constant between the first end and the second end; wherein the first side surface is disposed toward the bend, the first strain and the second strain varying between the first end and the second end within ranges of no more than 3% when the beam is compressed into the delivery configuration, and the first strain and the second strain being less than at least 4% between the first end and the second end when the beam is compressed into the delivery configuration.

The intraluminal device further comprising a second strain along the second side surface, the second strain being substantially constant between the first end and the second end, wherein the first side surface is disposed toward the bend, the first strain and the second strain varying between the first end and the second end within ranges of no more than 3% when the beam is compressed into a delivery configuration.

The intraluminal device wherein the cross-sectional area is varied without varying the material property, a first distance between the first side surface and the second side surface at the first end being greater than a second distance between the first side surface and the second side surface at the second end, a thickness of the beam being substantially constant between the first end and the second end.

The intraluminal device wherein the beam comprises a strut in a stent, the strut being made from a superelastic material.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
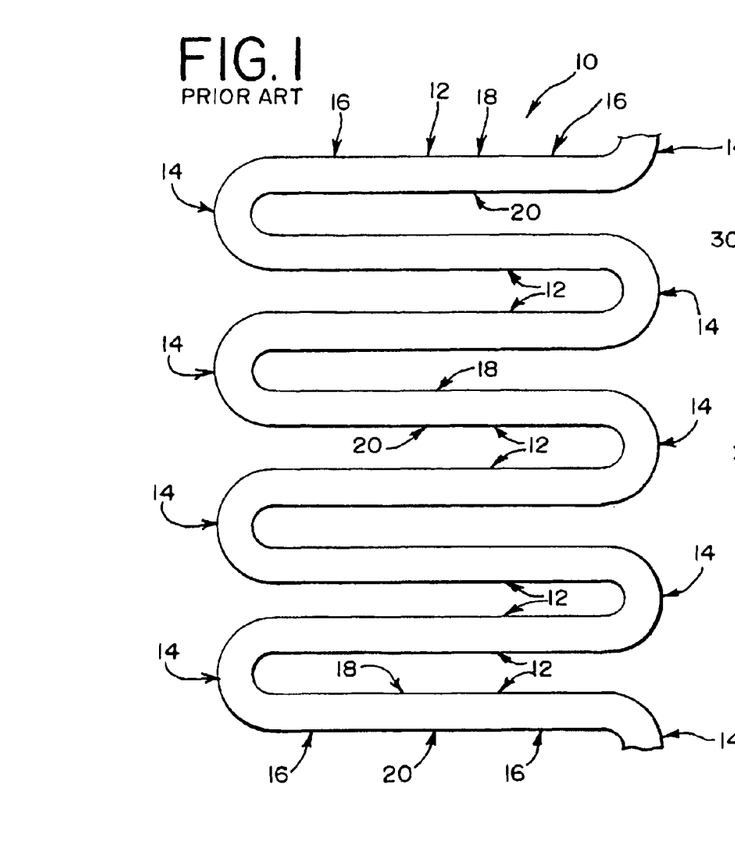
FIG. 1 is a plan view of a prior art stent structure.

Referring now to the drawings, and particularly to FIG. 1, a prior art stent structure 10 is shown. As is well known in the art, a stent structure 10 typically includes a series of struts 12, or beams 12, interconnected by a series of bends 14. Many different types of materials may be used to form stent structures like the structure 10 shown in FIG. 1. For example, in the case of self-expandable stents, it is normally preferred to use an elastic material like nitinol or stainless steel. One common manufacturing technique for making a stent structure 10 is laser cutting the structure 10 from a metal cannula. However, other known methods may also be used. As shown in FIG. 1, a bend 14 is connected to each end portion 16 of the struts 12, and different struts 12 are connected to each side of the bends 14. The bends 14 on opposing ends of each strut 12 face in opposite directions. The bends 14 and struts 12 may also be further connected to other struts and bends or other structures to form the desired length, diameter and geometry of a stent. For example, longitudinal struts may be used to interconnect the bends 14 and struts 12 to extend the structure along the entire length of the stent. The stent structure 10 shown in FIG. 1 is only one example of the type of stent structures that are possible, and many different stent structures or other structures for intraluminal devices may be formed using struts 12, or beams 12, like that shown here. In FIG. 1, a typical stent structure 10 that is well known to those in the art is shown in a collapsed, low profile configuration. In the low profile configuration, the included angle between adjacent struts 12 is normally less than 5°. This configuration would typically be used to thread the stent structure 10 through intravascular passageways to position the stent for implantation at a desired area for treatment. Typically, the stent is released at the site of implantation, and the stent structure 10 expands to a larger profile until the stent contacts the artery wall or other tissue structure.

The width of the struts 12 shown in FIG. 1 may be defined as the distance between the top side surface 18 and the bottom side surface 20 of each strut 12. As shown in FIG. 1, the width of the prior art struts 12 is constant along the length of the struts 12. Thus, the top side surface 18 and bottom side surface 20 are generally parallel to each other along the entire length of each strut 12. Many conventional stents are currently made with struts having uniform cross-sections like that shown here because of the simplicity of designing and manufacturing such structures. However, one disadvantage of struts 12 like this is that the strain in the stent structure 10 is concentrated in the bends 14 of the structure 10. Strain is introduced into a typical stent structure 10 during several stages of its use. For example, a relatively large strain is initially introduced into the stent structure 10 to compress the sent into a low profile configuration like that shown in FIG. 1. After the stent is released and implanted, the stent structure 10 remains permanently stressed under a lower, operational strain. Because the strain in conventional stent structures 10 is concentrated in the bends 14, the designs of most conventional stents must be limited in the range of expansion and compression that may be achieved, the length of struts that may be used and/or by other design considerations.

For example, most stent designs are limited by the elastic limit of the material used to make the structure of the stent. One material that is commonly used to make stents is nitinol. Nitinol is a preferred material because it is a superelastic material that can accommodate particularly high levels of strain without permanently deforming. Typically, the elastic limit of nitinol occurs at a strain level of about 10%. Nitinol achieves superior elasticity in part because the microstructure of nitinol in its relaxed, non-stressed state, consists of a mostly austenite structure. As strain is introduced into nitinol, the austenite microstructure begins to change to a martensite microstructure along the plateau region of the stress-strain curve. The elastic limit occurs where the austenite microstructure completely transforms to a martensite microstructure. If this is allowed to occur, the nitinol material will become permanently deformed and will not return to its original shape when the strain is relieved from the structure. The design of a stent is also limited by the fatigue limit of the material used. For example, in the case of nitinol, it is generally preferred to maintain operational strain cycles within a range of 0.4% or less to avoid possible fatigue failures.

Figure 2:
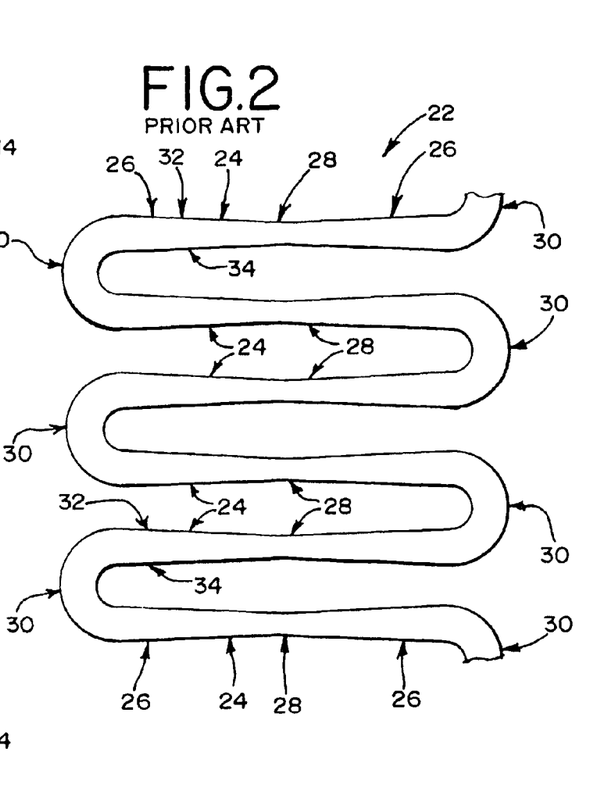
FIG. 2 is a plan view of another prior art stent structure.

An alternative prior art stent structure 22 is shown in FIG. 2. This stent structure 22 is described in U.S. Pat. No. 6,190,406 to Duerig et al. As shown, each strut 24 is formed by two end portions 26 connected together by a middle portion 28. The width of the end portions 26 is wider adjacent the bends 30 and is narrower adjacent the middle portion 28. As shown in FIG. 2 herein and described in Duerig et al., the taper of the end portions 26 may be a simple linear tapered reduction in width. Moreover, as shown in the figures of Duerig et al., both the top side surface 32 and the bottom side surface 34 of the end portions 26 are tapered at the same rate as each other. As descried in Duerig et al., the bending radius is kept constant in this design, and the bending of the end portions 26 is defined by the following formula:

$$1/R = 12FLI(ETW^3).$$

Duerig et al. concludes that the strut width should vary as the cube root of the distance from the end.

Figure 3A:
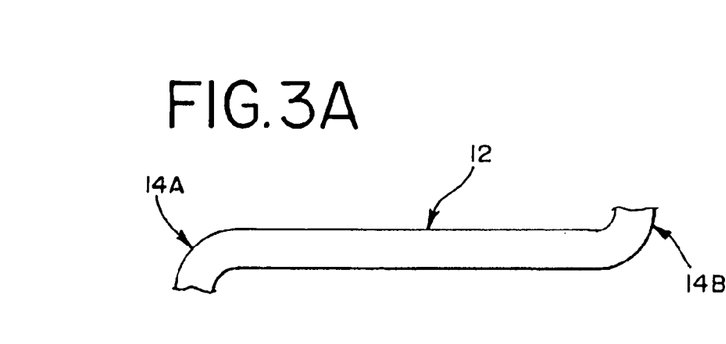
FIG. 3A is a plan view of a strut shown in FIG. 1, with the strut illustrated in a collapsed, low profile configuration.
Figure 3B:
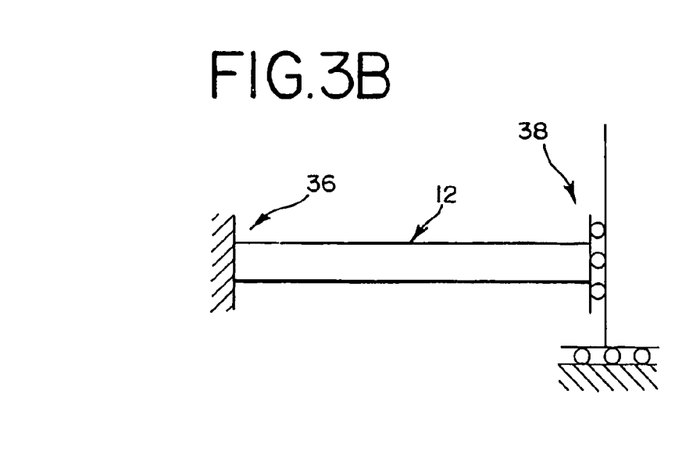
FIG. 3B is a free body diagram of the strut shown in FIG. 3A.
Figure 4A:
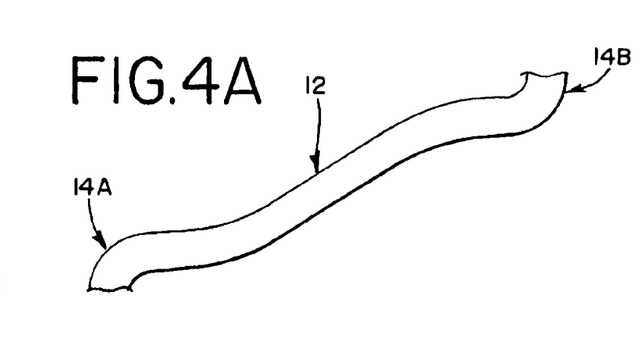
FIG. 4A is a plan view of the strut shown in FIG. 3A, with the strut illustrated in an expanded, larger profile configuration.
Figure 4B:
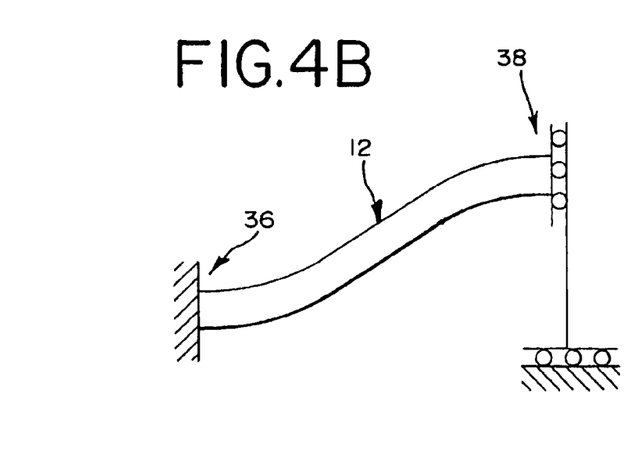
FIG. 4B is a free body diagram of the strut shown in FIG. 4A.

Turning to FIG. 3A, a strut 12 from the stent structure 10 shown in FIG. 1 is shown. The strut 12 is shown in this figure in a collapsed, low profile configuration. As shown, bends 14 facing in opposite directions are connected to opposing end portions 16 of the strut 12. A free body diagram of the strut 12 shown in FIG. 3A is shown in FIG. 3B. As shown, the left side bend 14A is represented by a rigid connection 36 and the right side bend 14B is represented by a flexible end 38 that is allowed to move both vertically and horizontally. In FIG. 4A the strut 12 is shown in a bent orientation to illustrate a typical angular orientation of the strut 12 when a stent is expanded to a larger profile configuration. A free body diagram of the strut 12 shown in FIG. 4A is shown in FIG. 4B. Like the free body diagram of FIG. 3B, the left side bend 14A of FIG. 4B is represented by a rigid connection 36, and the right side bend 14B is represented by a flexible end 38 that is allowed to move both vertically and horizontally.

Figure 5:
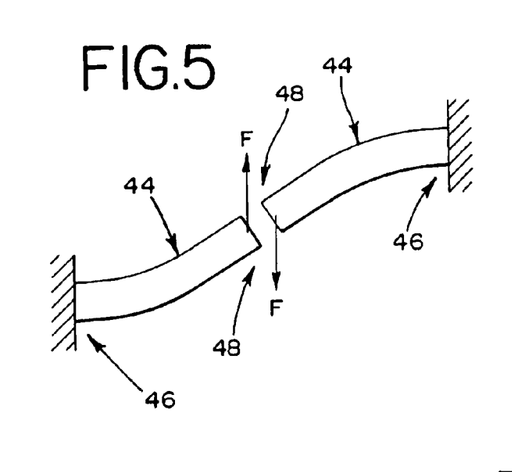
FIG. 5 is a simplified free body diagram of the strut shown in FIGS. 3A-4B.

Turning to FIG. 5, the free body diagram of the strut 12 shown in FIGS. 3A-4B may be simplified further. As shown, the free body diagram of the stent 12 may be simplified as two separate end portions 44 that are cantilevered from opposing rigid connections 46. The cantilevered end portions 44 are bent by equal but opposite vertical forces applied to the free ends 48 of each end portion 44.

Figure 6:
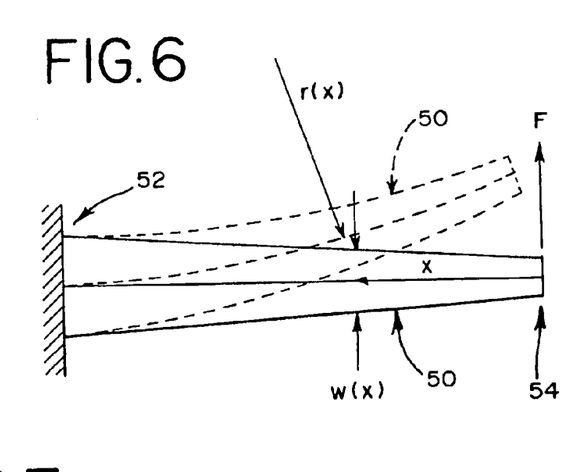
FIG. 6 is a free body diagram of one end portion of the strut shown in FIG. 5.

One way to improve the distribution of strain along the length of a strut is to taper the end portions so that the width of an end portion is wider adjacent the bend and narrower adjacent the middle portion. Thus, as shown in FIG. 6, the end portion 50 is wider adjacent the rigid connection 52 and narrower adjacent the free end 54. Assuming that the bending radius, r(x), is constant as Duerig et al. assumes, the bending of the end portion 50 may be defined by the formula:

$$1/r(x) = 12Fx/(Etw(x)^3) \quad \text{(Equation 1)}$$

where F is the applied force, x is the distance from the free end 54 of the cantilevered end portion 50, E is the Young's modulus, t is the thickness of the end portion 50, and w(x) is the width of the end portion 50 along the length of the end portion 50.

One problem with the end portion 50 shown in FIG. 6 and struts designed around Equation 1 is that the strain is not evenly distributed along the length of the end portion. An improvement would be to have the strain distributed substantially constant along the length of the top side surface and substantially constant along the length of the bottom side surface. To achieve this, it must be realized that the magnitude of the strain, e(x), along the top side surface and the bottom side surface may be defined by the formula:

$$e(x) = w(x)/(2r(x)). \quad \text{(Equation 2)}$$

Next, solving Equation 2 for 1/r(x) and substituting the result into Equation 1 results in the following formula:

$$2e(x)/w(x) = 12Fx/(Etw(x)^3). \quad \text{(Equation 3)}$$

Equation 3 may then be simplified into the following formula:

$$e(x) = 6Fx/(Etw(x)^2). \quad \text{(Equation 4)}$$

From Equation 4, it can be derived that the width of the end portion 50 should be proportional to the square root of the distance from the free end 54 of the end portion 50. Thus, this relationship is preferred to keep the strain substantially constant along the length of the top side surface and the bottom side surface of an end portion 50. Alternatively, the moment of inertia of the cross-section of the end portion 50 may be defined by the relationship of $I=tw(x)^2$. However, it is also contemplated that other relationships may also achieve improved strain distributions. For example, the width between the side surfaces may also be proportional to the distance from an end raised to a power between 0.6 and 0.4. More preferred, the width between the side surfaces may be proportional to the distance from an end raised to a power between 0.55 and 0.45. Moreover, either the top side surface or the bottom side surface may satisfy one of these relationships, or both side surfaces may satisfy one of the relationships. In addition, a substantially constant strain may be achieved by varying a section property of the end portion, including without limitation, the cross-sectional area, thickness or material type.

Figure 7:
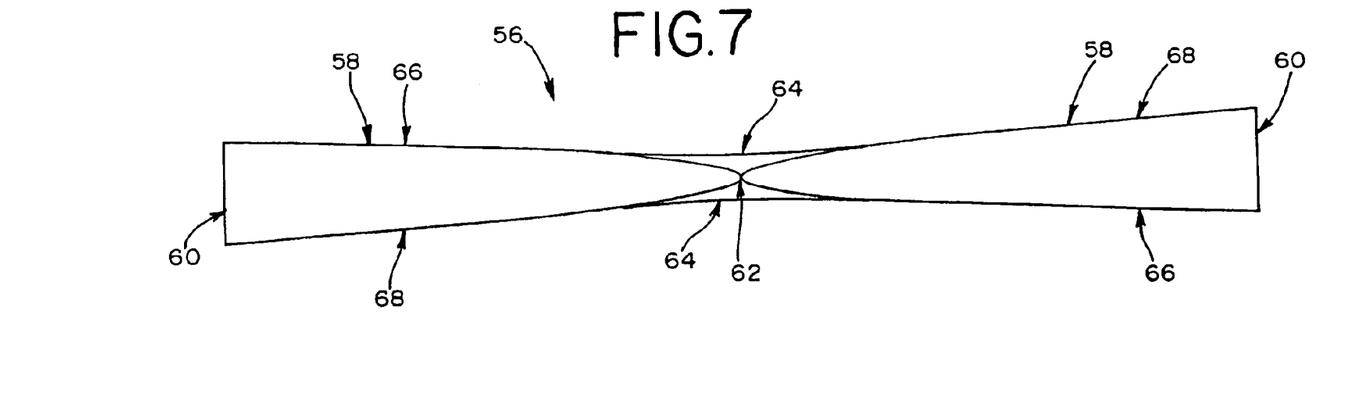
FIG. 7 is a plan view of an improved strut.

One embodiment of the improved strut 56 is shown in FIG. 7. The strut 56 shown in FIG. 7 has been designed to satisfy the relationship provided in Equation 4. The strut 56 includes two end portions 58 that are each connected to bends at the first end 60 of each end portion 58. As described above, the first end 60 was generally represented as a rigid connection in the free body diagrams. As shown in FIG. 7, the second ends 62 of each end portion may theoretically meet at a centerpoint. However, it is preferred that the two end portions 58 be connected together by a smoothly contoured middle portion 64. Therefore, the second ends 62 of each end portion 58 may be positioned in relationship to the middle portion 64 and adjacent thereto. The width of each end portion 58 is defined by the distance between the top side surface 66 and the bottom side surface 68 of each end portion 58. Thus, as shown, the width of the end portions 58 is wider adjacent the first end 60 of each end portion 58 and is narrower adjacent the middle portion 64. As described above, when a bending strain is introduced into the strut 56, the strain is distributed more evenly along the length of the strut 56 so that the strain is substantially constant along the length of each end portion 58.

Figure 8:
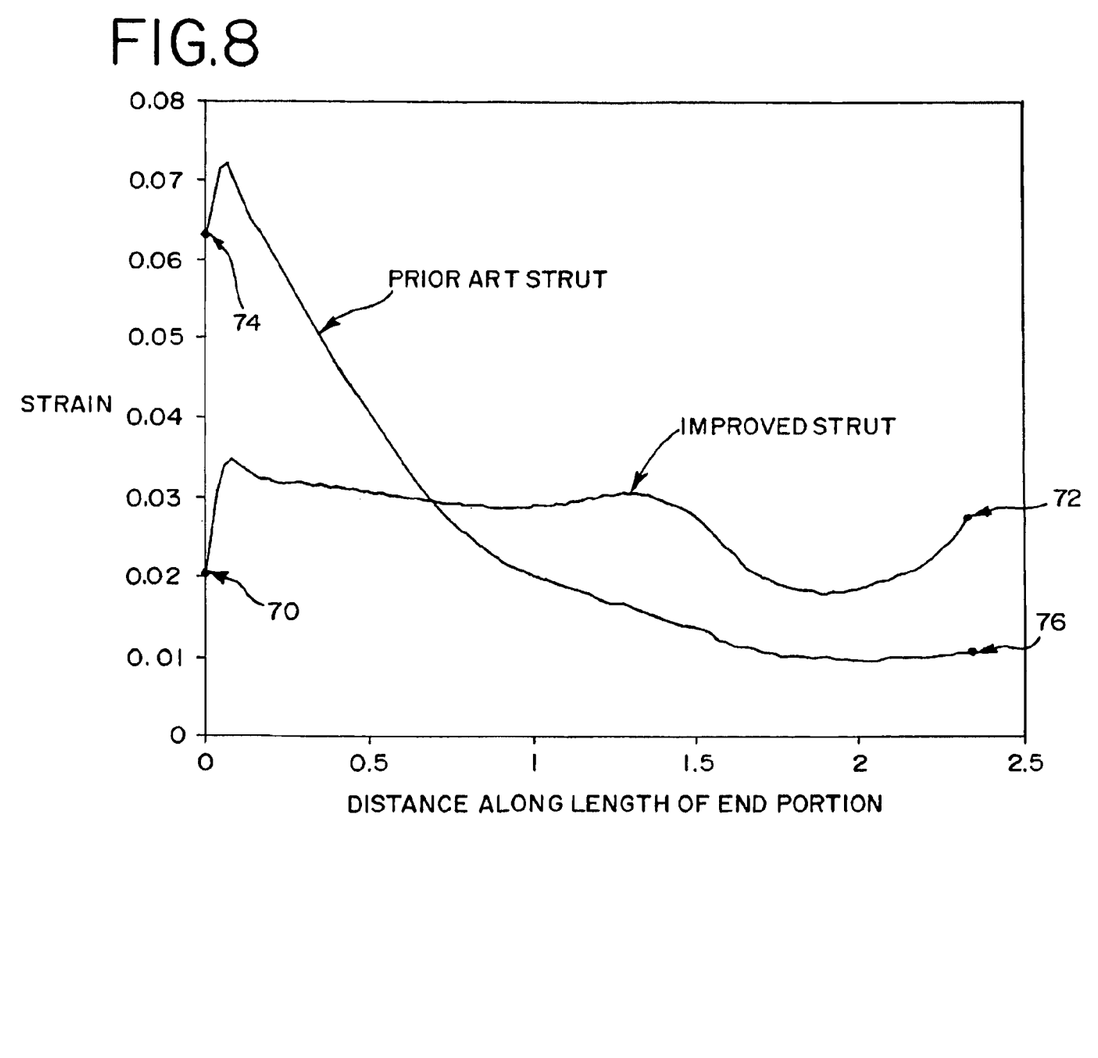
FIG. 8 is a chart showing strain levels along the end portion of a strut shown in FIG. 2 and the end portion of the strut shown in FIG. 7.

Turning to FIG. 8, a comparison of the strain distribution is provided for the improved strut 56 shown in FIG. 7 compared to the prior art strut 24 shown in FIG. 2. The strains shown in FIG. 8 represent the strain along the bottom side of each strut as illustrated in the example of FIG. 6. In general, this represents an area of maximum strain. However, the top side of the struts and other locations along the length of the struts may experience similar strain distributions. The maximum strains shown in FIG. 8 are generally representative of the strains that would be experienced by a strut when the stent is compressed into the delivery configuration. As shown, the strain level of the improved strut 56 is substantially constant between the first end 70 and the second end 72 of the end portions, where the first end 70 is generally representative of the first end 60 in FIG. 7, and the second end 72 is generally representative of the second end 62 in FIG. 7. Preferably, the strain varies between the first end 70 and the second end 72 within a range of no more than 3%. Further, the strain between the first end 70 and the second end 72 is preferably less than 4%. By reducing the strain level in the improved strut 56, the total range of operable strain may be maintained less than 0.4% after the stent has been delivered, thereby increasing the fatigue life of stents. By contrast, the strain distribution of the prior art strut 24 varies about twice as much as the improved strut 56. As shown, the strain reaches a peak in the prior art strut 24 near the first end 74 adjacent the bend. The strain then decreases sharply along the length of the end portion away from the first end 74. The strain is near the minimum strain level at the second end 76. The first end 74 in FIG. 8 is generally representative of the portion of the struts 24 in FIG. 2 near the bends 30, and the second end 76 in FIG. 8 is generally representative of the portion of the struts 24 in FIG. 2 near the middle portions 28. As shown, the maximum strain is more 7% at the peak. Moreover, the strain varies between the first end 74 and the second end 76 within a range of more than 6%.

The differences between the prior art and the invention are now readily apparent. As shown in FIG. 8, the strain level of prior art structures substantially varies along the length of the strut. By contrast, the strain level of the invention remains substantially constant along the length of the strut. In particular, with regard to the strut 56 shown in FIG. 7, the strain levels experienced by the top side surface 66 and the bottom side surface 68 will generally be different from each other when a bending force is applied to the strut 56. However, along the length of the bottom side surface 68, the strain level remains substantially constant from the first end 60 to the second end 62. This is generally represented by the strain level shown in FIG. 8 between the first end 70 and the second end 72. Similarly, the strain level along the length of the top side surface 66 in FIG. 7 remains substantially constant from the first end 60 to the second end 62. However, the substantially constant strain level of the top side surface 66 will generally be less than the strain level of the bottom side surface 68, assuming a bending force is applied as depicted in FIG. 6.

One of the advantages of the improved struts is that strain is distributed more evenly throughout the stent structure. In particular, strain levels may be redistributed away from the bends and distributed along the length of the struts. As a result, the maximum strain levels may be reduced. This may allow designers to optimize the expanded and collapsed diameters of a stent. For example, stent structures may be compressed to smaller collapsed diameters without permanently deforming or damaging the structure of the stent. Therefore, this may allow stents to be used in smaller passageways and may minimize the trauma of introducing stent delivery systems. In addition, because the stent may be designed with a smaller collapsed diameter, more annular space may be available between the stent and the restraining sheath positioned around the stent. This may allow additional coatings and/or graft materials to be attached to the outer diameter of the stent between the stent and the restraining sheath. Further, stents with wider expansion ratios may be designed to reduce the number of different stents that are needed to treat various conditions. In addition, stents may be designed with shorter struts to minimize tissue prolapse and increase radial force.

Another advantage of the improved struts is that the fatigue life of the stent structure may be increased. Fatigue life may be a concern with traditional stent structures since stents remain slightly compressed by the artery wall or other tissue structure even after implantation. This compression introduces an operational strain into the stent structure. Because a person's heart typically causes the arteries in the vascular system to expand and contract with each heartbeat, an implanted stent normally expands and contracts a small amount each time the heart beats. In conventional stent structures, this may cause a fatigue failure in the bends of the stent structure since the cycles of operational strain are concentrated in the bends. By contrast, the improved struts may reduce the risk of bend failures by minimizing the operational strain levels. In addition, stents may be designed to have greater axial flexibility and improved stretch characteristics.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with all embodiments of the invention.

We claim:

1. An intraluminal device, comprising:
   a beam comprising an end portion connected to a bend adjacent a first end and connected to a middle portion adjacent a second end, said beam and said bend being made from an elastic material;
   said end portion comprising a first side surface disposed toward said bend and a second side surface disposed away from said bend, said first side surface and said second side surface defining a width therebetween, wherein said width at said first end is greater than said width at said second end;
   an outer surface and an inner surface defining a thickness therebetween, wherein said thickness is constant from said first end to said second end; and
   wherein said width along a length from said second end to said first end is substantially proportional to a distance of said width from said second end raised to a power of 0.5, a first strain thereby being substantially constant along said first side surface between said first end and said second end.

2. The intraluminal device according to claim 1, wherein said beam comprises a strut in a stent.

3. The intraluminal device according to claim 1, wherein said beam is connected to another beam, said beams being collapsible into a delivery configuration adapted to pass through a lumen and a delivered configuration adapted to engage a wall of said lumen, an included angle defined between said beams being adapted to be less than 5° in said delivery configuration.

4. The intraluminal device according to claim 1, wherein said beam comprises a strut in a stent made from a superelastic material, said strut being connected to another strut, said struts being collapsible into a delivery configuration adapted to pass through a lumen and a delivered configuration adapted to engage a wall of said lumen, an included angle defined between said struts being adapted to be less than 5° in said delivery configuration.

5. The intraluminal device according to claim 1, wherein said first strain is less than at least 4% between said first end and said second end when said beam is compressed into a delivery configuration.

6. The intraluminal device according to claim 1, wherein said beam is connected to another beam, said beams being collapsible into a delivery configuration adapted to pass through a lumen and expandable to a delivered configuration adapted to engage a wall of said lumen, an included angle defined between said beams being adapted to be less than 5° in said delivery configuration, further comprising a second strain along said second side surface, said second strain being substantially constant between said first end and said second end, and a total range of operable strain for said first strain and said second strain being less than 0.4% in said delivered configuration.

7. The intraluminal device according to claim 1, wherein said beam comprises a strut in a stent made from a superelastic material, said strut being connected to another strut, said struts being collapsible into a delivery configuration adapted to pass through a lumen and a delivered configuration adapted to engage a wall of said lumen, an included angle defined between said struts being adapted to be less than 5° in said delivery configuration, further comprising a second strain along said second side surface, said second strain being substantially constant between said first end and said second end, said first strain and said second strain varying between said first end and said second end within ranges of no more than 3% when said beam is compressed into said delivery configuration, said first strain and said second strain being less than at least 4% between said first end and said second end when said beam is compressed into said delivery configuration, and a total range of operable strain for said first strain and said second strain being less than 0.4% in said delivered configuration.

8. The intraluminal device according to claim 1, wherein said beam comprises two like end portions, a first end portion connected to a first said bend adjacent said first end and connected to said middle portion adjacent said second end, and a second end portion connected to a second said bend adjacent said first end and connected to said middle portion adjacent said second end.

9. The intraluminal device according to claim 8, wherein said beam comprises a strut in a stent made from a superelastic material, said strut being connected to another strut, said struts being collapsible into a delivery configuration adapted to pass through a lumen and a delivered configuration adapted to engage a wall of said lumen, an included angle defined between said struts being adapted to be less than 5° in said delivery configuration, further comprising a second strain along said second side surface, said second strain being substantially constant between said first end and said second end, said first strain and said second strain varying between said first end and said second end within ranges of no more than 3% when said beam is compressed into said delivery configuration, said first strain and said second strain being less than at least 4% between said first end and said second end when said beam is compressed into said delivery configuration, and a total range of operable strain for said first strain and said second strain being less than 0.4% in said delivered configuration.

* * * * *